(12) United States Patent
Yu et al.

(10) Patent No.: US 8,044,215 B2
(45) Date of Patent: Oct. 25, 2011

(54) METHODS FOR THE PREPARATION OF AMPHILLIC NITROGEN CONTAINING IMIDAZOLINIUM DERIVATIVE COMPOUNDS

(75) Inventors: Cheng-Sein Yu, Chesterfield, MO (US); Lee B. Bussey, San Mateo, CA (US)

(73) Assignee: Juvaris BioTherapeutics, Inc., Pleasanton, CA (US)

( * ) Notice: Subject to any disclaimer, the term of this patent is extended or adjusted under 35 U.S.C. 154(b) by 239 days.

(21) Appl. No.: 12/432,660

(22) Filed: Apr. 29, 2009

(65) Prior Publication Data

US 2010/0280258 A1    Nov. 4, 2010

(51) Int. Cl.
*C07D 233/22*    (2006.01)
(52) U.S. Cl. .................................. 548/350.1; 548/352.1
(58) Field of Classification Search ............... 548/350.1, 548/352.1
See application file for complete search history.

(56) References Cited

U.S. PATENT DOCUMENTS

| 5,264,618 A | 11/1993 | Felgner et al. |
| 5,705,655 A * | 1/1998 | Heath et al. ................ 548/350.1 |
| 5,830,878 A | 11/1998 | Gorman et al. |

FOREIGN PATENT DOCUMENTS

| WO | WO 96/40962 A1 | 12/1996 |
| WO | WO 9640962 A1 * | 12/1996 |
| WO | WO 99/25342 A1 | 5/1999 |
| WO | WO 9925342 A1 * | 5/1999 |

OTHER PUBLICATIONS

Solodin et al., Biochemistry, (1995), vol. 34, p. 13,537-13544 (disclosed by Applicants).*
Baghbanzadeh et al., Aus. J. Chem., (2009), vol. 62, p. 244-249 (disclosed by Applicants).*
Solodin et al., Biochemistry, (1995), vol. 34, pp. 13,537-13544 (disclosed by Applicants).*
Baghbanzadeh et al., Aus. J. Chem., (2009), vol. 62, pp. 244-249 (disclosed by Applicants).*
Solodin, et al., "A novel series of amphiphilic imidazolinium compounds for in vitro and in vivo gene delivery" Biochemistry, American Chemical Society 34:13537-13544 (1995).
Goncalves, E., et al., "The effect of liposome size on the final lipid/DNA ratio of cationic lipoplexes", Biophysical Journal 86:1554-1563 (2004).
Baghbanzadeh, M., et al., "Can molecular sieves be used as scavangers in microwave chemistry?" Aust. J. CHem., 62:244-249 (2009).

* cited by examiner

*Primary Examiner* — Yong Chu
(74) *Attorney, Agent, or Firm* — Sughrue Mion, PLLC

(57) ABSTRACT

The disclosure provides new methods for preparing nitrogen-containing amphiphiles and their use in the preparation of liposomes and other lipid-containing carriers of pharmaceutical substances, including nucleic acids used in gene therapy.

21 Claims, No Drawings

METHODS FOR THE PREPARATION OF AMPHILLIC NITROGEN CONTAINING IMIDAZOLINIUM DERIVATIVE COMPOUNDS

FIELD OF THE DISCLOSURE

The disclosure relates to new methods for preparing nitrogen-containing amphiphiles and their use in the preparation of liposomes and other lipid-containing carriers of pharmaceutical substances, including nucleic acids used in gene therapy.

BACKGROUND OF THE DISCLOSURE

Liposomes are one of a number of lipid-based materials used as biological carriers and have been used effectively as carriers in a number of pharmaceutical and other biological situations, particularly to introduce drugs, radiotherapeutic agents, enzymes, viruses, transcriptional factors and other cellular vectors into a variety of cultured cell lines and animals. Successful clinical trials have examined the effectiveness of liposome-mediated drug delivery for targeting liposome-entrapped drugs to specific tissues and specific cell types. For example, U.S. Pat. No. 5,264,618 describes a number of techniques for using lipid carriers, including the preparation of liposomes and pharmaceutical compositions and the use of such compositions in clinical situations, the disclosure of which is hereby incorporated by reference in its entirety for all purposes. While the basic methodology for using liposome-mediated vectors is well developed, improvements in the materials used in the methods, both in terms of biocompatibility and in terms of effectiveness of the carrier process, are still desirable.

In particular, the expression of exogenous genes in humans and/or various commercially important animals will ultimately permit the prevention and/or cure of many important human diseases and the development of animals with commercially important characteristics. Genes are high molecular weight, polyanionic molecules for which carrier-mediated delivery usually is required for DNA transfection of cells either in vitro or in vivo. Therefore, it is of interest to develop lipid transfection vectors which will enhance both the delivery and the ultimate expression of the cloned gene in a tissue or cell of interest. Since in some instances a treatment regimen will involve repeated administration of a gene (or other pharmaceutical product), it also is of interest that the lipid carriers be nontoxic to the host, even after repeated administration.

Amphiphilic imidazolinium derivatives, such as 1-acyloxyethyl-2-alkyl(alkenyl)-3-hydroxyethylimidazolinium derivatives, and methods for their preparation and their use as cationic amphiphiles have been described in U.S. Pat. Nos. 5,705,655 and 5,830,878, the disclosures of each are hereby incorporated by reference in their entirety for all purposes. These cationic amphiphiles form complexes with nucleic acids and other biological compounds, and their nucleic acid complexes are capable of transforming mammalian cells. Due to the success of these derivatives, what is needed are improved methods for preparing and purifying these compounds. These methods need to be scalable and capable of routinely producing highly pure compounds.

SUMMARY OF THE DISCLOSURE

New methods for the preparation of biodegradable, amphiphilic imidazolinium derivatives are provided. These cationic amphiphiles are capable of forming complexes with nucleic acids and other biological compounds, and the nucleic acid complexes are capable of transforming mammalian cells.

Thus, in one embodiment, the disclosure provides methods preparing a compound of formula (I):

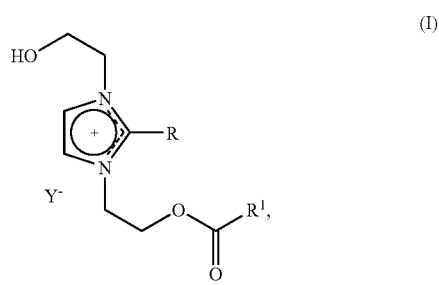

by heating a compound of formula (II) between about 30° C. to about 60° C. in a trihaloalkyl/alcohol solvent, and in the presence of 2-5 A molecular sieves (pore size 2-5 Å), to produce the compound of formula (I):

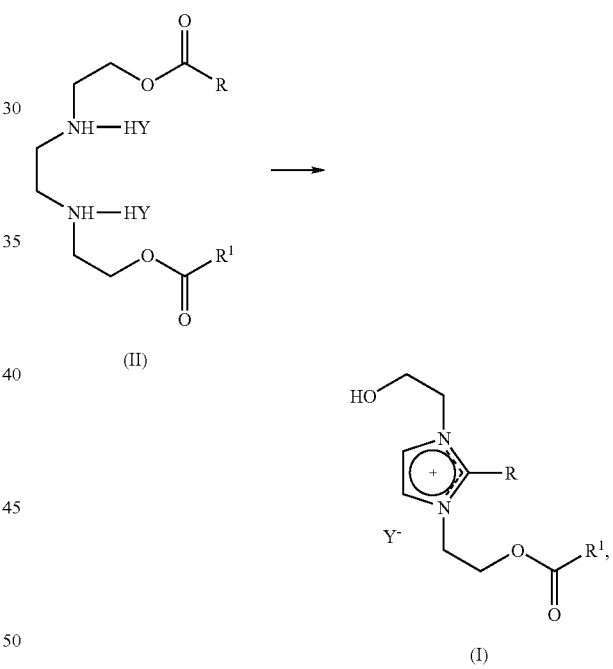

wherein: R and $R^1$ are each independently a $C_{11}$-$C_{29}$ straight-chain, aliphatic hydrocarbyl group; and Y is a halogen, acetate, succinate or citrate. Additional embodiments feature the use of 3-4 A molecular sieves (pore size 3-4 (pore size Å). Another embodiment features the use 4 A molecular sieves (pore size 4 Å).

DESCRIPTION OF THE DISCLOSURE

Definitions

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'—represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

An "alkylesteryl," as used herein, refers to a moiety having the formula R'—C(O)O—R", wherein R' is an alkylene moiety and R" is an alkyl moiety.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkyl" or "cycloalkylalkyl" also refers to a 3 to 7 membered cycloalkyl group attached to the remainder of the molecule via an unsubstituted alkylene group. Recitation of a specific number of carbon atoms (e.g. C$_1$-C$_{10}$ cycloalkylalkyl) refers to the number of carbon atoms in the alkylene group.

The term "heterocycloalkyl" or "heterocycloalkylalkyl" also refers to a 3 to 7 membered heterocycloalkyl group attached to the remainder of the molecule via an unsubstituted alkylene group. Recitation of a specific number of carbon atoms (e.g. C$_1$-C$_{10}$ hetero-cycloalkylalkyl) refers to the number of carbon atoms in the alkylene group.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The phrase "aliphatic hydrocarbyl" refers to monovalent groups consisting generally of carbon and hydrogen. Thus, aliphatic hydrocarbyl groups include alkyl, alkenyl and alkynyl groups (in both straight and branched chain forms), carbocyclic groups (including polycycloalkyl groups such as bicyclooctyl and adamantyl) and aryl groups, and combinations of the foregoing, such as alkylcycloalkyl, alkylpolycycloalkyl, alkylaryl, alkenylaryl, alkynylaryl, cycloalkylaryl and cycloalkenylaryl groups. Thus, the phrase "aliphatic hydrocarbyl" includes, but are not limited to paraffins and alkenyls, for example: methyl, ethyl, propyl, n-butyl, tert-butyl, sec-butyl, isobutyl, amyl, isoamyl, hexyl, cyclohexyl, heptyl, octyl, nonyl, decyl, dodecyl, 2-ethylhexyl, pentenyl, butenyl, and the like. Other examples of aliphatic hydrocarbyl groups include, but are not limited to alkyl, cycloalkyl, alkenyl, cycloalkenyl, alkynyl, alkadienyl, cyclic, and the like, and includes all unsubstituted, substituted, branched, cyclic and combinations or derivatives thereof, in each instance having from 1 to about 30 carbon atoms.

Similarly, the phrase "aliphatic hydrocarbylene" refers to divalent groups corresponding to the monovalent aliphatic hydrocarbyl groups described above. The phrase "di-valent aliphatic hydrocarbyl" refers to an aliphatic hydrocarbyl group that possesses two points of attachment to the rest of the molecule.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. Substituents for each of above noted aryl and heteroaryl ring systems are selected from the group of acceptable substituents described below. The terms "arylene" and "heteroarylene" refer to the divalent derivatives of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From above discussion of substituents, one of skill in art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The compounds of the disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogen-phosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by the disclosure and are intended to be within the scope of the disclosure.

Certain compounds of the disclosure possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the disclosure may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the disclosure, whether radioactive or not, are encompassed within the scope of the disclosure.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolyl-sulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the disclosure contain both basic and acidic functionalities that allow the compounds to be converted into either base or acid addition salts.

In addition to salt forms, the disclosure relates to compounds, which are in a prodrug form. Prodrugs of the compounds described herein are those compounds that readily undergo chemical changes under physiological conditions to provide the compounds of the disclosure. Additionally, prodrugs can be converted to the compounds of the disclosure by chemical or biochemical methods in an ex vivo environment. For example, prodrugs can be slowly converted to the compounds of the disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, physiological conditions.

The terms "treating" or "treatment" in reference to a particular disease includes prevention of the disease.

The symbol ⁓ denotes the point of attachment of a moiety to the remainder of the molecule.

The compounds of the present invention may be synthesized using one or more protecting groups generally known in the art of chemical synthesis. The term "protecting group" refers to chemical moieties that block some or all reactive moieties of a compound and prevent such moieties from participating in chemical reactions until the protective group is removed, for example, those moieties listed and described in Greene, et al., Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking or protecting groups include, for example:

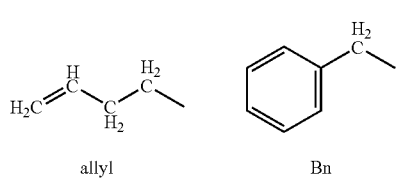

allyl    Bn

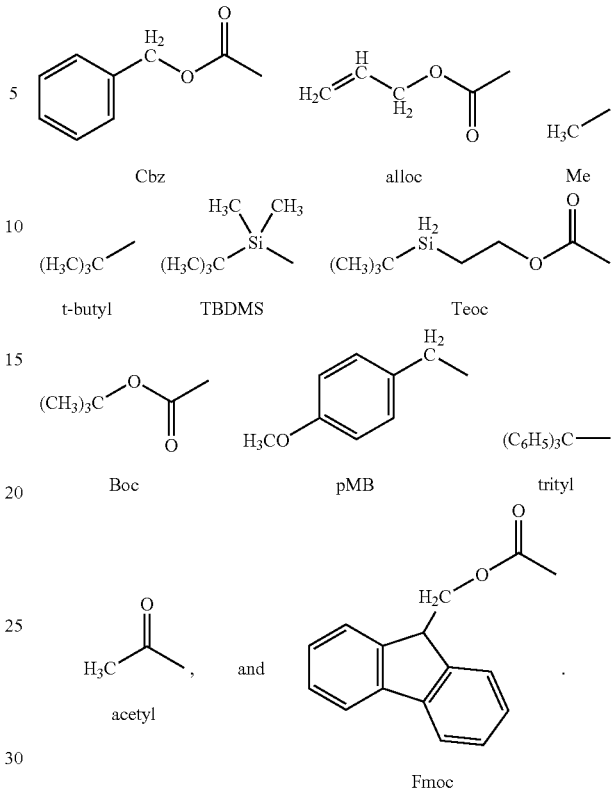

Methods for the Preparation of Amphiphilic Imidazolinium Derivatives

New methods for the preparation of metabolizable amphiphilic imidazolinium derivatives are provided, which are useful as carriers for biologically active molecules such as antibiotics or nucleic acids used in cell transformation processes. The use of the amphiphilic materials as nucleic acid carriers has been described in detail, since the compositions prepared using the amphiphiles are particularly efficacious for this purpose. The amphiphiles are also useful in standard drug delivery regimens, such as for the delivery of antibiotics to the lungs of a patient.

It is apparent that the cations must be present in association with one or more anions, e.g., hydroxide, chloride, or bromide ions or more complex organic anions or bases. The synthetic techniques described below for producing the amphiphiles initially creates a hydroxide salt of the cationic amphiphile. However, the particular anion associated with an amphiphilic cation is not critical to the formation or utility of the amphiphilic cation and may exchange (in whole or part) for other anions during use of the composition. Alternatively, the anion can be deliberately exchanged, such as by dissolving the initially formed salt (or an intermediate salt) in the presence of an excess of a salt containing the desired anion. Accordingly, the disclosed amphiphilic compounds are described in this specification generally in terms of the cation without reference to any particular anion. A number of specific examples of anions are given, as well as general guidance for the selection of anions. For human administration, chloride, bromide or other physiologically acceptable anions including acetate, succinate and citrate may be used. The cations are either nontoxic themselves, and/or they yield by-products, for example, enzymatic cleavage products, which are nontoxic to a host organism or which are endogenous to a host organism. Generally, both the original lipids and their degradation products are nontoxic to a host organism.

The disclosure particularly relates to new methods for preparing a compound of formula (I):

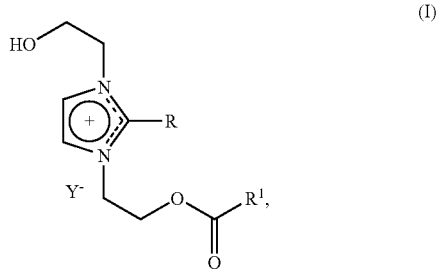

by heating a compound of formula (II) between about 30° C. to about 60° C. in a trihaloalkyl/alcohol solvent, and in the presence of 4 A molecular sieves, to produce the compound of formula (I):

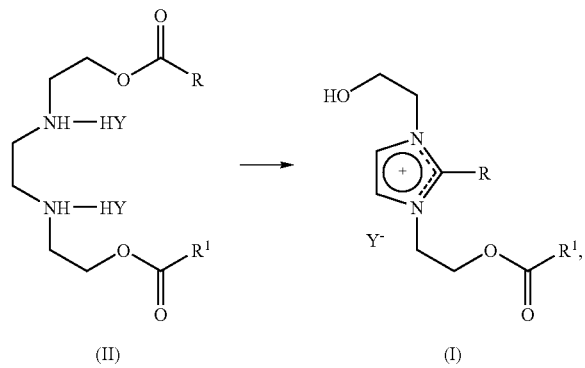

wherein R and $R^1$ are each independently a $C_{11}$-$C_{29}$ straight-chain, aliphatic hydrocarbyl group; and $Y^-$ is a halogen, acetate, succinate or citrate.

The disclosed compounds of formula (I) may be synthesized using new and improved methods for a rearrangement reaction starting from N,N-bis(2-hydroxyethyl)ethylenediamine through an amino-protected diacylated intermediate and an amino-deprotected diacylated intermediate having formula (II), to the desired product of formula (I). In other embodiments, the disclosure provides methods for preparing compounds of formula (I), wherein R and $R^1$ each independently have from about 1 to about 30 carbon atoms inclusive. The R and $R^1$ groups may be saturated or are unsaturated having one or more ethylenically unsaturated linkages and are suitably the same or are different from each other. Illustrative $R^1$ groups together with the —CO— group to which it is attached (i.e., $R^1$—CO—) include lauroyl, myristoyl, palmitoyl, stearoyl, linoleoyl, eicosanoyl, tricosanoyl and nonacosanoyl (derived from the fatty acids of the corresponding name: lauric, myristic, etc.). When given system names for the $R^1$ groups alone, the corresponding names of the aliphatic hydrocarbyl group derived from lauric acid is undecyl; from myristic acid, tridecyl; from palmitic acid, pentadecyl; from stearic acid, heptadecyl; from linoleic acid, cis,cis-8,11-heptadecydienyl; from eicosanoic acid, nonadecyl; from tricosanoic acid, dicosanyl; and from triacontanoic acid, nonacosanyl. Illustrative R groups may be identical to the listed $R^1$ groups, as they are generally derived from the same fatty acids. Illustrative cations include is 1-[2-(9-(Z)-octadecenoyloxy)ethyl]-2-[8-(Z)-heptadecenyl]-3-(2-hydroxyethyl)imidazolinium. Other illustrative cations of the above formula (I) will be apparent from the formula and the different permutations of above meanings of R and $R^1$.

In another aspect the disclosure provides methods for preparing a compound of formula (I), by heating a compound of formula (II) between about 30° C. to about 60° C. in a trihaloalkyl/alcohol solvent, and in the presence of 4 A molecular sieves, wherein R and $R^1$ are each:

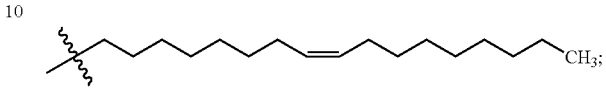

and Y is chloro.

In another aspect the disclosure provides methods for preparing a compound of formula (I), by heating a compound of formula (II) between about 30° C. to about 60° C. in a trihaloalkyl/alcohol solvent, and in the presence of 4 A molecular sieves, wherein the trihaloalkyl/alcohol solvent is about a 4:1 v/v mixture.

In another aspect the disclosure provides methods for preparing a compound of formula (I), by heating a compound of formula (II) between about 30° C. to about 60° C. in a trihaloalkyl/alcohol solvent, and in the presence of 4 A molecular sieves, wherein the trihaloalkyl solvent is chloroform or bromoform; and the alcohol solvent is methanol, ethanol, propanol, or isopropanol or combinations thereof.

In another aspect the disclosure provides methods for preparing a compound of formula (I), by heating a compound of formula (II) between about 30° C. to about 60° C. in a trihaloalkyl/alcohol solvent, and in the presence of 4 A molecular sieves, wherein the trihaloalkyl solvent is chloroform; and the alcohol solvent is methanol.

In another aspect the disclosure provides methods for preparing a compound of formula (I), by heating a compound of formula (II) between about 30° C. to about 60° C. in a trihaloalkyl/alcohol solvent, and in the presence of 4 A molecular sieves, wherein the 4 A molecular sieves is present in about a 1:1 to about a 3:1 w/w ratio of 4 A molecular sieves/compound of formula (II).

In another aspect the disclosure provides methods for preparing a compound of formula (I), by heating a compound of formula (II) between about 30° C. to about 60° C. in a trihaloalkyl/alcohol solvent, and in the presence of 4 A molecular sieves, wherein the 4 A molecular sieves is present in about a 1:2 w/w ratio of 4 A molecular sieves/compound of formula (II).

In another aspect the disclosure provides methods for preparing a compound of formula (I), by heating a compound of formula (II) between about 30° C. to about 60° C. in a trihaloalkyl/alcohol solvent, and in the presence of 4 A molecular sieves, wherein the compound of formula (II) is heated to about 55° C. for about 4 to about 24 hours.

In another aspect the disclosure provides methods for preparing a compound of formula (I), by heating a compound of formula (II) between about 30° C. to about 60° C. in a trihaloalkyl/alcohol solvent, and in the presence of 4 A molecular sieves, further comprising purifying the compound of formula (I) by silica gel chromatography and recrystallization from acetone.

In another aspect the disclosure provides methods for preparing a compound of formula (I), by heating a compound of formula (II) between about 30° C. to about 60° C. in a trihaloalkyl/alcohol solvent, and in the presence of 4 A molecular sieves, wherein the compound of formula (I) has formula (III):

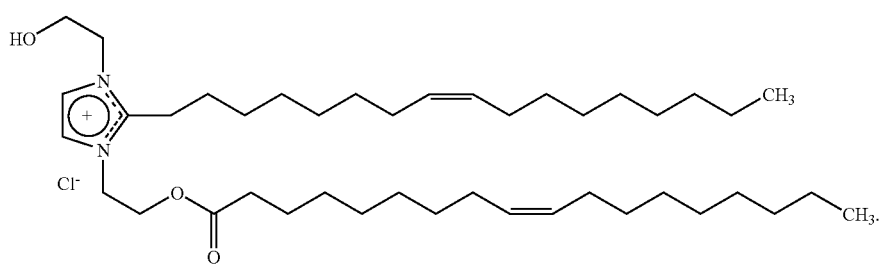

(III)

In another aspect the disclosure provides the compound of formula (III), prepared by the method for preparing a compound of formula (I), by heating a compound of formula (II) between about 30° C. to about 60° C. in a trihaloalkyl/alcohol solvent, and in the presence of 4 A molecular sieves.

The general synthetic method for preparing the compound of formula (I) is shown in the following reaction scheme:

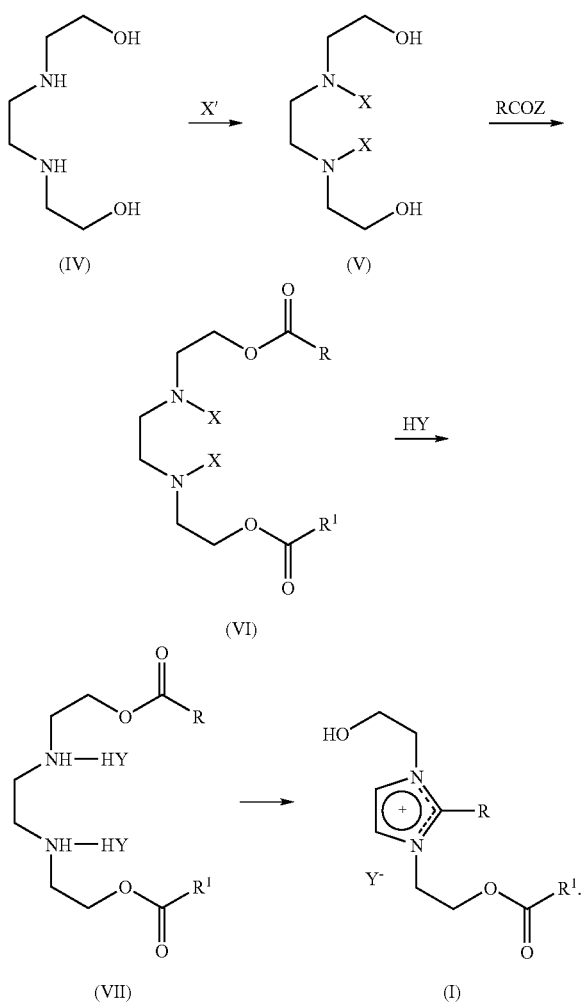

In the above scheme, X is any amino protecting group that reacts with and protects a secondary amino group in the presence of a hydroxyl group, while being capable of being removed by acid hydrolysis (e.g., with a strong acid such as HCl); X' is the precursor of the X protecting group (e.g., an anhydride or acid halide where the protecting group is an acyl group); RCOZ is an anhydride or acid halide in which R is the same R (or $R^1$) that has been previously defined; and HY is a strong acid (e.g., sulfuric acid or one of its derivatives or a hydrogen halide such as hydrochloric acid) or weak acid (e.g., acetic acid, succinic acid or citric acid, and the like). In one embodiment, the amino protecting group X is t-butyloxycarbonyl (BOC) prepared from di-t-butyl-dicarbonate; the acylating group is an acid chloride of one of the fatty acids previously named and described above; and the acid for the deprotection and rearrangement steps (which may be combined into a single step) is HCl.

Heat for the rearrangement reaction may be provided by refluxing the reactants in a solvent or mixture of solvents, having a boiling point ranging from about 30° C. to about 60° C., or from about 40° C. to about 60° C., or from about 50° C. to about 60° C. Useful solvents for the rearrangement reaction include, but are not limited to, mixtures of trihaloalkyl/alcohol solvents such as 1:1; 2:1; 3:1, and 4:1 v/v mixtures of trihaloalkyl solvents such as chloroform, bromoform, or iodoform; and alcohol solvents such as methanol, ethanol, propanol, or isopropanol, respectively, and in the presence of molecular sieves.

The rearrangement reaction may also occur in the presence of molecular sieves. A molecular sieve is a material containing tiny pores of a precise and uniform size that is used as an adsorbent for gases and liquids, including water. Molecules small enough to pass through the pores are adsorbed while larger molecules are not. It is different from a common filter in that it operates on a molecular level. For instance, a water molecule may be small enough to pass through while larger molecules are not. Because of this, molecular sieves may function as a desicant and thus, help drive the rearrangement reaction. A molecular sieve can adsorb water up to 22% of its own weight. Molecular sieves may consist of aluminosilicate minerals, clays, porous glasses, microporous charcoals, zeolites, active carbons, or synthetic compounds that have open structures through which small molecules, such as nitrogen and water can diffuse. 3 A molecular sieves (pore size 3 Å): adsorbs $NH_3$, $H_2O$, (not $C_2H_6$); and 4 A molecular sieves adsorbs $H_2O$, $CO_2$, $SO_2$, $H_2S$, $C_2H_4$, $C_2H_6$, $C_3H_6$, and $C_2H_5OH$. In some embodiments, mixtures of 3 A and 4 A molecular sieves may be used. In additional embodiments 2-5 A molecular sieves (pore size 2-5 Å) may be used. While additional embodiments feature the use 4 A molecular sieves (pore size 4 Å).

The initial imidazolinium ion formed may be the hydroxide salt and/or chloride salt (if prepared using HCl as the acid), but the anion (counter ion) may be replaced by exchange as previously described.

Thus, in another aspect the disclosure provides methods for preparing a compound of formula (I):

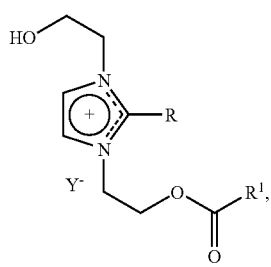

(I)

comprising the steps of:
a) protecting the secondary amino groups in the compound of formula (IV) to provide the compound of formula (V):

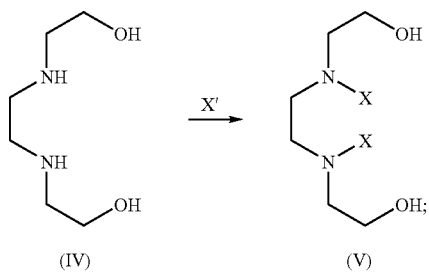

b) protecting the primary alcohol groups in the compound of formula (V) to provide the compound of formula (VI):

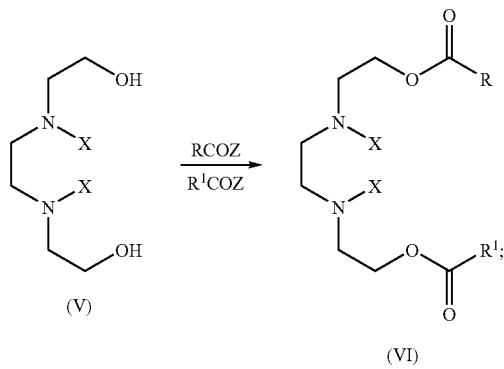

c) deprotecting the compound of formula (VI) to provide the compound of formula (II):

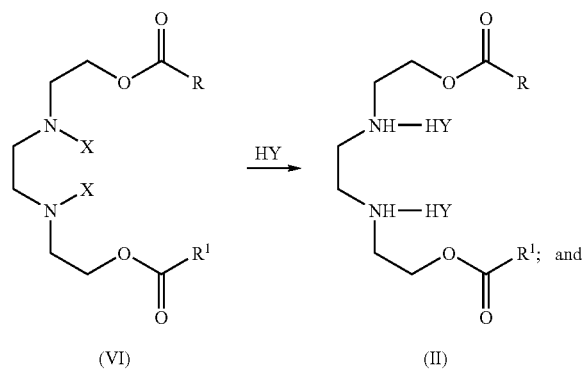

d) heating the compound of formula (II) between about 30° C. to about 60° C. in a trihaloalkyl/alcohol solvent, and in the presence of 4 A molecular sieves, to produce the compound of formula (I):

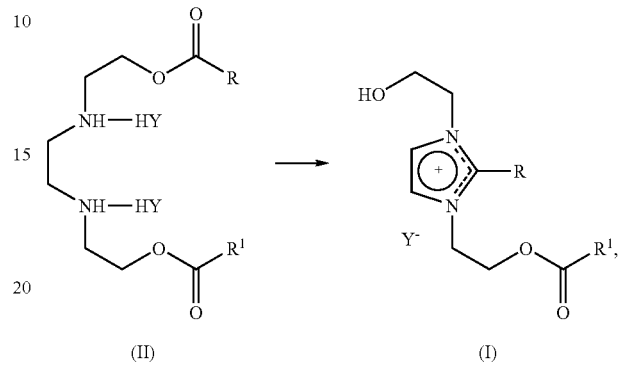

wherein R and $R^1$ are each independently a $C_{11}$-$C_{29}$ straight-chain, aliphatic hydrocarbyl group; X' is di-tert-butyldicarbonate (($BOC)_2O$); X is tert-butyloxycarbonyl (BOC); Y is a halogen, acetate, succinate or citrate; and Z is OCOR or $OCOR^1$.

In another aspect, the disclosure provides methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (I), wherein R and $R^1$ are each:

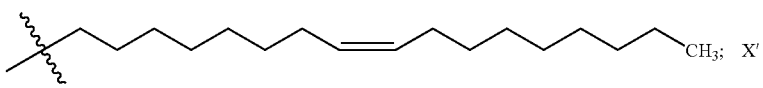

is di-tert-butyldicarbonate (($BOC)_2O$); X is tert-butyloxycarbonyl (BOC); Y is chloro; and Z is OCOR or $OCOR^1$.

In another aspect, the disclosure provides methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (I), wherein R and $R^1$ are each independently a $C_{11}$-$C_{29}$ straight-chain, aliphatic hydrocarbyl group; X' is di-tert-butyldicarbonate (($BOC)_2O$); X is tert-butyloxycarbonyl (BOC); Y is a halogen, acetate, succinate or citrate; and Z is OCOR or OCOR$^1$, and wherein the trihaloalkyl/alcohol solvent is about a 4:1 v/v mixture.

In another aspect, the disclosure provides methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (I), wherein R and R$^1$ are each independently a $C_{11}$-$C_{29}$ straight-chain, aliphatic hydrocarbyl group; X' is di-tert-butyldicarbonate ((BOC)$_2$O); X is tert-butyloxycarbonyl (BOC); Y is a halogen, acetate, succinate or citrate; and Z is OCOR or OCOR$^1$, wherein the trihaloalkyl/alcohol solvent is about a 4:1 v/v mixture, and wherein the trihaloalkyl solvent is chloroform or bromoform; and the alcohol solvent is methanol, ethanol, propanol, or isopropanol.

In another aspect, the disclosure provides methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (I), wherein R and R$^1$ are each independently a $C_{11}$-$C_{29}$ straight-chain, aliphatic hydrocarbyl group; X' is di-tert-butyldicarbonate ((BOC)$_2$O); X is tert-butyloxycarbonyl (BOC); Y is a halogen, acetate, succinate or citrate; and Z is OCOR or OCOR$^1$, wherein the trihaloalkyl/alcohol solvent is about a 4:1 v/v mixture, and wherein the trihaloalkyl solvent is chloroform; and the alcohol solvent is methanol.

In another aspect, the disclosure provides methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (I), wherein R and R$^1$ are each independently a $C_{11}$-$C_{29}$ straight-chain, aliphatic hydrocarbyl group; X' is di-tert-butyldicarbonate ((BOC)$_2$O); X is tert-butyloxycarbonyl (BOC); Y is a halogen, acetate, succinate or citrate; and Z is OCOR or OCOR$^1$, and wherein the 4 A molecular sieves is present in about a 1:1 to about a 3:1 w/w ratio of 4 A molecular sieves/compound of formula (II).

In another aspect, the disclosure provides methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (I), wherein R and R$^1$ are each independently a $C_{11}$-$C_{29}$ straight-chain, aliphatic hydrocarbyl group; X' is di-tert-butyldicarbonate ((BOC)$_2$O); X is tert-butyloxycarbonyl (BOC); Y is a halogen, acetate, succinate or citrate; and Z is OCOR or OCOR$^1$, and wherein the 4 A molecular sieves is present in about a 1:2 w/w ratio of 4 A molecular sieves/compound of formula (II).

In another aspect, the disclosure provides methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (I), wherein the compound of formula (II) is heated to about 55° C. for about 4 to about 24 hours.

In another aspect, the disclosure provides methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (I), further comprising purifying the compound of formula (I) by silica gel chromatography and recrystallization from acetone.

In another aspect, the disclosure provides methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (I), wherein the compound of formula (I) has formula (III):

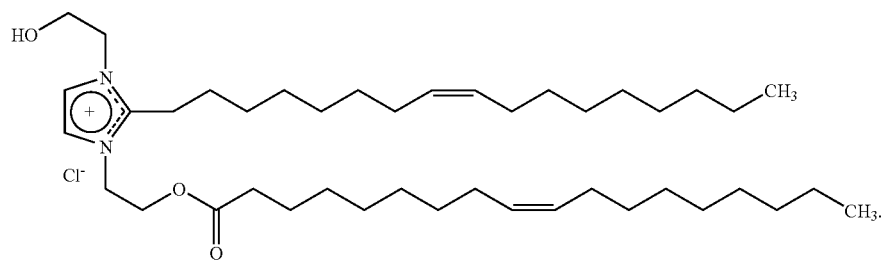

(III)

In another aspect, the disclosure provides the compound of formula (III), prepared by the methods for preparing a compound of formula (I) by: a) protecting the secondary amino groups in the compound of formula (IV) to provide the compound of formula (V); b) protecting the primary alcohol groups in the compound of formula (V) to provide the compound of formula (VI); c) deprotecting the compound of formula (VI) to provide the compound of formula (II); and d) heating the compound of formula (II) between about 30° C. to about 60° C. in a trihaloalkyl/alcohol solvent, and in the presence of 4 A molecular sieves, to produce the compound of formula (III).

The rearrangement reaction and the ensuing overall synthesis need not be restricted to production of the specified cationic amphiphiles. Instead, it represents a general synthesis of imidazolinium compounds of the formula (VII):

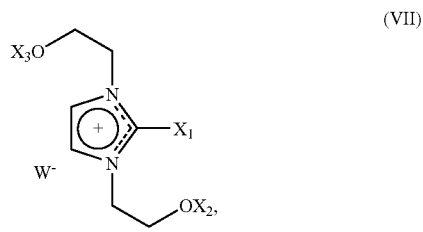

(VII)

wherein $X_1$ represents the residue of an acyl group after the rearrangement reaction as shown (from H to a complex organic group) while $X_2$ and $X_3$ each independently represent H or an organic group. $X_2$ may initially represent R—CO—, but this group may be removed and/or be replaced by a different organic group using standard chemical reactions. Since one of the two potential hydroxyl groups in the initial product is already protected, synthesis of compounds in which $X_2$ and $X_3$ represent different groups may readily be accomplished. W may be any anion from a strong or weak acid, including but not limited to, halogen, acetate, succinate or citrate.

Ions in which both $X_2$ and $X_3$ represent H are useful as these can be used in the synthesis of numerous imidazolinium compounds. Although there is no particular limit on the structure of the three "X" groups in the general synthesis other than those imposed by solubility or reactivity under the heating conditions being used for the reaction (which will be readily apparent), organic groups that are hydrocarbyl groups containing 30 or fewer carbons and their oxygenated products (especially fatty acids and their reaction products as previously described, as well as other hydrocarbyl groups and oxygenated products containing 15 or fewer carbon atoms, or 10 or fewer carbon atoms, or hydrocarbyl groups containing no more than one phenyl ring with the remainder of the hydrocarbyl group being composed of alkyl groups, especially alkyl groups of 5 or fewer carbons). Organic groups formed from oxygenated hydrocarbyl groups may be carboxylic acids, alcohols, esters, ethers, ketones and aldehydes containing no more than one such functional group per organic group. Examples of imidazolinium ions that can be prepared by the synthesis as described above (with further modification of the hydroxyl groups using simple organic reactions) include 1,3-dihydroxy-ethylimidazolinium, 1-methoxyethyl-3-hydroxy-ethylimidazolinium, 1-hydroxyethyl-2-phenyl-3-methylcarboxyethylimidazolinium, 1,3-dimethoxyethoxy-ethylimidazolinium, 1,3-hydroxyethyl-2-tridecylimidazolinium, and 1-hydroxyethyl-2-cis,cis-8,11-heptadecyldienyl-3-oleoyloxyethylimidazolinium.

The rearrangement reaction is a self condensation reaction with the elimination of water. However, the solvent and/or other reaction conditions may be of importance to the overall reaction. Solvents and/or reaction conditions that drive the reaction to completion without affecting the yield of product are particularly useful. As described above, mixtures of trihaloalkyl/alcohol solvents at moderate temperatures (e.g., 50° C. to 60° C.) in the presence of molecular sieves (3 A or 4 A) are particularly useful. If an acid catalyst is used in addition to speed up the progress of the reaction, these protic solvents may provide easier proton exchange.

The disclosed cationic lipids are typically useful as carriers for various biological molecules, such as antibiotics or nucleic acids. In particular, the cationic lipids may be used alone or combined with other lipids in formulations for the preparation of lipid vesicles or liposomes for use in intracellular delivery systems. Uses contemplated for the disclosed cationic lipids include transfection procedures corresponding to those presently known that use amphiphilic lipids, including those using commercial cationic lipid preparations, such as Lipofectin™, and various other published techniques using conventional cationic lipid technology and methods. The disclosed cationic lipids may be used in pharmaceutical formulations to deliver therapeutic agents by various routes and to various sites in an animal body to achieve a desired therapeutic effect. When considering cell transfection as the intended use, it has been determined that the free hydroxyl group of the imidazolinium ion should not be acylated with an additional fatty acid groups, as such "tri fatty acid" have been found not to be effective in transforming cells.

Because such techniques are generally known in the art, background information and basic techniques for the preparation of pharmaceutical compositions containing lipids will not be repeated at this time. A reader unfamiliar with this background information is referred to the publications under the heading Relevant Literature above and further to U.S. Pat. No. 5,264,618, the disclosure of which is hereby incorporated by reference in its entirety for all purposes. This patent describes a number of therapeutic formulations and methods in detail, including examples of the use of specific cationic lipids (different from those described here) that can be followed in detail by substituting the disclosed cationic lipids for those described in the patent. The disclosed compositions may minimally be useable in the manner described in the patent, although operating parameters may need to be modified in order to achieve optimum results, using the specific information provided for the disclosed compounds in this specification along with the knowledge of a person skilled in the arts of lipid preparation and use.

The following examples are offered by way of illustration and not by way of limitation.

EXAMPLES

The following examples are offered to illustrate, but not to limit the claimed invention. The preparation of embodiments of the present invention is described in the following examples. Those of ordinary skill in the art will understand that the chemical reactions and synthesis methods provided may be modified to prepare many of the other compounds of the present invention. Where compounds of the present invention have not been exemplified, those of ordinary skill in the art will recognize that these compounds may be prepared by modifying synthesis methods presented herein, and by using synthesis methods known in the art.

Example 1

Synthesis of 1-[2-(9(Z)-octadecenoyloxy)ethyl]-2-[8(Z)-heptadecenyl)-3-(2-hydroxyethyl)imidazolinum chloride (III)

1-[2-(9(Z)-octadecenoyloxy)ethyl]-2-[8(Z)-heptadecenyl)-3-(2-hydroxyethyl)imidazolinum chloride (III) is synthesized by the following four-step reaction sequence:

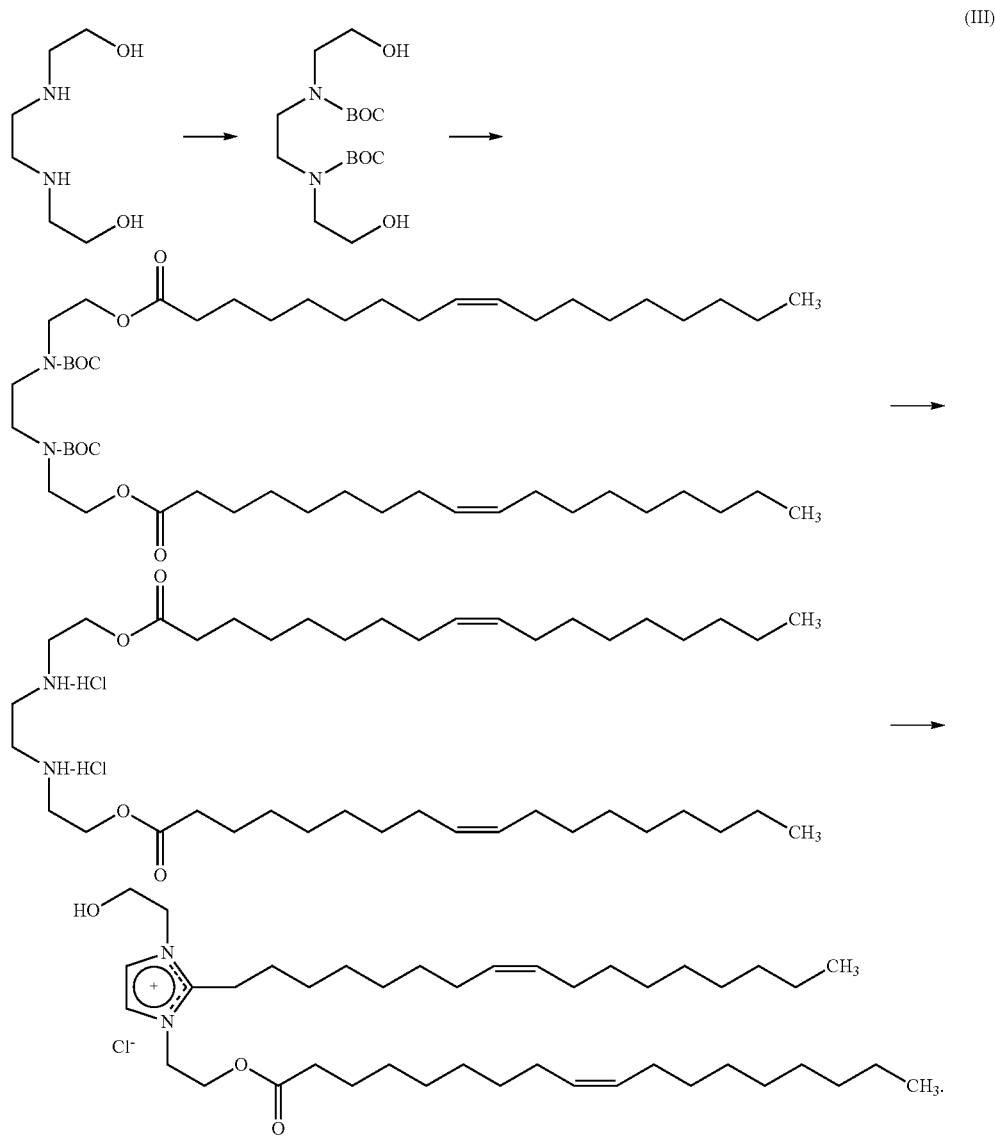

(III)

Step 1: Preparation of N,N'-Di-BOC-N,N'-bis(2-hydroxyethyl)ethylenediamine

The product was prepared by treating N,N'-bis(2-hydroxyethyl)ethylenediamine in methanol with (BOC)$_2$O at room temperature. The reaction mixture was chilled to −15° C. to −20° C. to precipitate the product. After filtration, the precipitate was desiccated to yield the product.

Step 2: Preparation of N,N'-Di-BOC-N,N'-bis(2-hydroxyethyl)ethylenediamine dioleoyl ester Esterification of N,N'-Di-BOC-N,N'-bis(2-hydroxyethyl) ethylenediamine with oleic acid in the presence of N,N'-dicyclohexylcarbodiimide (DCC), 4-dimethylaminopyridine (DMAP) and heptane at room temperature followed by filtration to remove the 1,3-dicyclohexylurea (DCU) and evaporation of the filtrate gave the crude N,N'-Di-BOC-N,N'-bis(2-hydroxyethyl)ethylenediamine dioleoyl ester. The crude product was used in next step without further purification.

Step 3: Preparation of N,N'-bis(2-hydroxyethyl)ethylenediamine dioleoyl ester•2 HCl BOC deprotection of the crude product from step 2 using 4.0 M HCl in 1,4-dioxane followed by filtration and rinsing the filter cake with CH$_2$Cl$_2$ afforded N,N'-bis(2-hydroxyethyl)ethylenediamine dioleoyl ester•2 HCl.

Step 4: Preparation of 1-[2-(9(Z)-octadecenoyloxy)ethyl]-2-[8(Z)-heptadecenyl]-3-(2-hydroxyethyl)imidazolinum chloride (III)

Refluxing a solution of N,N'-bis(2-hydroxyethyl)ethylenediamine dioleoyl ester•2 HCl in chloroform-methanol (4:1 v/v) in the presence of molecular sieves and purification by column chromatography yielded the desired product. The product was further purified by crystallization from acetone using a dry ice/acetone bath.

Example II

Process Flow Chart or the Synthesis of 1-[2-(9(Z)-octadecenoyloxy)ethyl]-2-[8(Z)-heptadecenyl)-3-(2-hydroxyethyl)imidazolinum chloride 1. Mix N,N'-bis(2-hydroxyethyl)ethylenediamine in methanol, then add di-tert-butyldicarbonate and stir at room temperature for 2 hrs.
2. Keep the mixture in freezer until inner temperature reaches ~−15° C., whereupon a precipitate forms.
3. Filter and rinse the precipitate with cold methanol (~−15° C.) followed by desiccation (high vacuum, ~45° C. overnight) to give N,N'-Di-BOC-N,N'-bis(2-hydroxyethyl)ethylenediamine.
4. Mix N,N'-Di-BOC-N,N'-bis(2-hydroxyethyl)ethylenediamine with oleic acid, N,N'-dicyclohexylcarbodiimide and 4-dimethylaminopyridine in n-heptane at room temperature for about 4-5 hrs.
5. Filter the mixture to remove dicyclohexylurea and rinse the filter cake with n-heptane. Evaporate the filtrate to dryness. Add fresh n-heptane, mix and filter again. Evaporate the filtrate to a light yellow oil to provide crude N,N'-Di-BOC-N,N'-bis(2-hydroxyethyl)-ethylenediamine dioleoyl ester.
6. Dissolve the crude N,N'-Di-BOC-N,N'-bis(2-hydroxyethyl)-ethylenediamine dioleoyl ester in 1,4-dioxane, then add 4M HCl in dioxane. Stir at room temperature for about 2-3 hrs to form a precipitate.
7. Filter and rinse the precipitate with 1,4-dioxane and dichloromethane. Desiccate the solids at room temperature under high vacuum to yield N,N'-bis(2-hydroxyethyl)ethylene-diamine dioleoyl ester•2HCl.
8. Heat the N,N'-bis(2-hydroxyethyl)ethylene-diamine dioleoyl ester•2HCl to about 50° C. in chloroform-methanol (4:1 v/v) in the presence of molecular sieves. Purify the reaction mixture with silica gel column chromatography using chloroform-methanol mixture as the eluent. Evaporation of the pure fractions gives the desired product: 1-[2-(9(Z)-octadecenoyl-oxy)ethyl]-2-[8-(Z)-heptadecenyl)-3-(2-hydroxyethyl)imidazolinium chloride (III). The product is further purified by crystallization from acetone using a dry ice/acetone bath.

Example III

Preparation of 1-[2-(9(Z)-octadecenoyloxy)ethyl]-2-[8(Z)-heptadecenyl)-3-(2-hydroxyethyl)-imidazolinum chloride (III)

Step 1: Preparation of N,N'-Di-BOC-N,N'-bis(2-hydroxyethyl)ethylenediamine

1. Set up a 500 ml 3-neck round bottom flask in a water bath and equipped as follows: a magnetic stirrer, a pressure-equalizing dropping funnel, a drying tube and a thermometer.
2. Prepare di-tert-butyldicarbonate, i.e. (BOC)$_2$O solution by melting (BOC)$_2$O in a ~60° C. water bath then weighed 164.58 g (0.76 M) and dissolve in methanol (72 ml).
3. Add N,N'-bis(2-hydroxyethyl)ethylenediamine (53.3 g, 0.36 M) and methanol (172 ml) to the flask.
4. Stir at about 22° C. for 20 minutes. Then the mixture is a suspension. Note: Temperature drops to about 12° C. after mixing for a few minutes.
5. Add the (BOC)$_2$O solution from step 2 slowly and control temperature at 30±10° C. during the addition. Caution! CO$_2$ gas is generated (exothermic reaction). Note: The addition takes 40 minutes. The product starts to precipitate after adding ~⅓ volume of the solution.
6. Rinse the (BOC)$_2$O container with methanol (25 ml) into the flask.
7. Suction the water in the water bath away and stir at ~20-25° C. for 2 hr.
8. Check the progress of the reaction with thin layer chromatography (TLC) (Silica Gel, chloroform-methanol 4:1 v/v, I$_2$-vapor and sulfuric-methanol 1:1 v/v spray/charred). TLC sample: 100 μl of the reaction mixture was diluted with 100 μl of methanol and spotted 5 μl on a TLC plate. Both starting materials were spotted on the same TLC plate as standards. The reaction is completed when no starting material and no mono-BOC protected product shows on TLC.
9. Keep product in a freezer until inner temperature reached ~−15° C. Allow product to stay at this temperature for ~1-2 hr. Note: The mixture was kept in the freezer (−20° C.) for about four hours before filtration. Do not keep in freezer overnight, some impurities will precipitate.
10. Filter and rinse with cold methanol (100 ml, ~−15° C.). Note: The color stays with the filtrate.
11. Desiccate at ~45° C. under high vacuum overnight to yield a white solid. H$^1$NMR spectrum confirmed the structure. Yield: 106 g (84.6%). The purity of the product was ~98% with ~1.5% impurity at origin and <0.5% impurity at solvent front. Note: The product was used in next step reaction without further purification. It should be almost free of methanol.

Step 2: Preparation of N,N'-Di-BOC-N,N'-bis(2-hydroxyethyl)ethylenediamine dioleoyl ester 1. Set up a 2 L-3-neck round bottom flask in a water bath, and equipped as follows: a grounded air driven stirrer, a pressure-equalizing dropping funnel, a thermometer, and a drying tube.
2. Add oleic acid (182 g, 0.644 M), N,N'-Di-BOC-N,N'-bis(2-hydroxyethyl)ethylenediamine (102 g, 0.293 M), DMAP (7.8 g, 0.0644 M), and heptane (600 ml) to the flask, and stir gently at room temperature.
3. Add a solution of DCC (132 g, 0.64 M) in heptane (300 ml) slowly within ~20 minute period. Rinse the DCC container with heptane (50 ml) into the flask. Temperature should be kept at 30±10° C. during DCC addition.
4. Stir at 25±5° C. and check the progress of the reaction with TLC (Silica Gel, chloroform-methanol 99:1 v/v, I$_2$-vapor and sulfuric acid-methanol 1:1 v/v spray/charred). Note: The reaction is completed in ~4-8 hrs.
5. Filter using glass microfibre filter paper over Whatman #54 paper in a Buchner funnel to remove DCU when the reaction completed. Rinsed the residue with heptane (300 ml). Note: Desiccate the DCU at ~50° C. under high vacuum overnight to form a white solid (141.38 g, 98.5% recovery).
6. Evaporate the filtrate at 40-45° C. under high vacuum to a hazy light yellow oil (292.9 g).
7. Add heptane (500 ml) to the oil and mix. Note: More DCU precipitates.
8. Filter using glass microfibre filter paper over Whatman #54 paper in a Buchner funnel to yield 1.6 g of DCU after desiccation. Total DCU recovery was 142.98 g (99.6% recovery).
9. Evaporate the filtrate under high vacuum in a 40-45° C. water bath to form a clear and light yellow oil (292 g, >100%). Purity was ~90% by TLC with oleic acid and DMAP as the major impurities. Note: The crude product was used in Step 3 reaction.

Step 3. Preparation of N,N'-bis(2-hydroxyethyl)ethylenediamine dioleoyl ester•2 HCl 1. Set up a 3 L-3-neck round bottom flask in a water bath equipped with a grounded air-driven stirrer, a temperature probe, and a drying tube.
2. Add N,N'-Di-BOC-N,N'-bis(2-hydroxyethyl)ethylenediamine dioleoyl ester (250 g) and 1,4-dioxane (250 ml) to the flask and allowed to mix for a few minutes.
3. With stirring, add 4M HCl in 1,4-dioxane in two portions (2×250 ml) all at once. Note: No noticeable CO$_2$ gas generation is observed right after the addition.
4. Stir at room temperature until no more starting material left. Monitor the progress of the reaction with TLC (Silica Gel, chloroform-methanol 4:1 v/v, $I_2$-vapor and/or sulfur acid-methanol 1:1 v/v spray/charred). Note: The mixture becomes very hazy after mixing for 6 minutes. A lot of foam forms after mixing for 20 minutes. The reaction is usually completed in 2-3 hrs.

5. Filter using Whatman #54 filter paper (diameter: 150 mm) in a Buchner funnel into a 4 L filtering flask and rinse the filter cake with 1,4-dioxane (350 ml), and then rinse with $CH_2Cl_2$ (1 L). Note: TLC shows that the major impurities, i.e. oleic acid/ester and DMAP, stay with the filtrate.

6. Desiccate at room temperature under high vacuum overnight to yield white solids (179.34 g, 95%). NMR ($H^1$) consistent with structure. The purity of the product was ~98% (Rf 0.8) with two slowly moving impurities at Rf 0.4 1-[2-(9(Z)-octadecenoyloxy)ethyl]-2-[8(Z)-heptadecenyl)-3-(2-hydroxyethyl)-imidazolinum chloride (III)) and Rf 0.2 1-[2-(9(Z)-octadecenoyloxy)ethyl]-2-[8(Z)-heptadecenyl)-3-(2-hydroxyethyl)-imidazolinum chloride (III)).

Step 4: Preparation of 1-[2-(9(Z)-octadecenoyloxy) ethyl]-2-[8(Z)-heptadecenyl)-3-(2-hydroxyethyl)- imidazolinum chloride (III)

A. 2.5 g Scale:
1. Setup a 100-ml round bottom flask equipped with a heating mantle, a reflux condenser and a drying tube.
2. Add chloroform-methanol 4:1 v/v (25 ml), N,N'-bis(2-hydroxyethyl)ethylenediamine dioleoyl ester•2 HCl (2.5 g) and molecular sieves (3.5 g).
3. Heat to reflux and continued to reflux until the reaction is ≧95% completion. Check the progress of the reaction with TLC (Silica Gel, chloroform-methanol 4:1 v/v, $I_2$-vapor and/or sulfur acid-methanol 1:1 v/v spray/charred). Note: It usually needs to reflux overnight (≧16 hrs). It is recommended to reflux under a nitrogen blanket.
4. Filter using Whatman glass microfibre filter on the top of Whatman #54 filter paper in a Buchner funnel and rinse the flask and filter cake with chloroform-methanol 4:1 v/v (25 ml).
5. Evaporate to dryness under high vacuum in a 35±5° C. water bath to form a light yellow oil.
6. Dissolve the oil in chloroform (5 ml) and charge onto Biotage Silica Gel pre-packed cartridge (Flush 40+M0827-1).
7. Rinse the flask with chloroform three times (3×2.5 ml) and charge to the cartridge.
8. Attach the compression module and then elute under ≦20 psi at flow rate of ~25 ml/min with chloroform-methanol 97.5:2.5 v/v (300 ml), 95:5 (300 ml), 92.5:7.5 (300 ml), 9:1 (300 ml), 85:15 (300 ml), and 8:2 (300 ml).
9. Check the purity of the individual fractions with TLC (Silica Gel, $CHCl_3$-methanol 4:1 v/v, $I_2$ vapor and/or 5% sulfuric acid in ethanol spray/charred).
10. The fractions with purity ≧99% are pooled and evaporate to a light yellow oil.
11. Dissolve the pure product in $CH_2Cl_2$ (10 ml) and filter through Millipore 0.22 μm membrane filter (Type GV) in a filter assemblies (250 ml capacity).
12. Rinse with dichloromethane (10 ml).
13. Evaporate under house vacuum and then under high vacuum in a 30±5° C. water bath to form a light yellow foaming semisolid (2 g, >85%). NMR is consistent with structure. Note: Release vacuum when too much foam forms and then pull vacuum again. Repeat the procedure a few times until no new foam forms.
14. Store in the Freezer at −20° C. or below.

B. 40 g Scale
1. Set up a 1 L-3-neck round bottom flask equipped with a heating mantle, a reflux condenser and a drying tube.
2. Add chloroform-methanol 4:1 v/v (400 ml), N,N'-bis(2-hydroxyethyl)ethylenediamine dioleoyl ester•2HCl (40.0 g) and molecular sieves (60.0 g).
3. Heat to reflux and continue to reflux until the reaction is ≧95% complete. Check the progress of the reaction with TLC (Silica Gel, chloroform-methanol 4:1 v/v, $I_2$-vapor and/or 5% sulfur acid in ethanol spray/charred). Note: It usually needs to reflux overnight (≧16 hrs). It is recommended to reflux under a nitrogen blanket.
4. Filter using Whatman glass microfibre filter on the top of Whatman #54 filter paper in a Buchner funnel and rinse the flask and filter cake with chloroform-methanol 4:1 v/v (200 ml).
5. Evaporate to dryness under high vacuum in a 35±5° C. water bath to form a light yellow oil (40 g).
6. Dissolve the oil in chloroform (60 ml) and charge onto a dry Silica Gel column (660 g, 391484, 07708CE).
7. Rinse the flask with chloroform three times (3×20 ml) and charge to the column.
8. Elute (gravity) with chloroform (1 L), chloroform-methanol 97.5:2.5 v/v (2 L), 95:5 (2 L), 92.5:7.5 (2 L), 9:1 (2 L), 85:15 (2 L), and 8:2 (2 L). Note: First fraction: 600 ml; 2nd fraction: 550 ml; 3rd fraction: 550 ml; 4th to 8th fractions: 400 ml; 9th to 73th fractions: 120 ml. The desired product starts to elute at chloroform-methanol 92.5:7.5 v/v step.
9. Check the purity of the individual fractions with TLC (Silica Gel, chloroform-methanol 4:1 v/v, $I_2$-vapor and/or 5% sulfuric acid in ethanol spray/charred).
10. The fractions (fractions 20 to 59) with purity ≧99% are pooled and evaporate to a light yellow oil (~35 g, not very dry yet).
11. Dissolve the pure product in dichloromethane (70 ml) and filtered through Millipore 0.22 μm membrane filter (Type GV) in a filter assemblies (250 ml capacity).
12. Rinse with dichloromethane three times (3×20 ml).
13. Evaporate under house vacuum and then under high vacuum in a 30±5° C. water bath to form a light yellow foaming semisolid (30.86 g, >85%). Note: Release vacuum when too much foam forms and pull vacuum again. Repeat the procedure a few times until no new foam form.
14. Dissolve the product in acetone (300 ml) and chill in a dry ice/acetone bath for ~2-3 hrs.
15. Filter using a dry ice pre-cooled fritted glass funnel (Kimax, 350 ml, ~−80° C.). Note: A spatula was used to scrape the precipitate sticking on the wall of the flask.
16. Rinse the flask and filter cake with dry ice pre-cooled acetone (50 ml). Note: The combined filtrate from Step 14 and washing from this step is evaporated to form a light yellow film (0.38 g, 1.2%). TLC (Silica Gel, chloroform-methanol 4:1 v/v, $I_2$-vapor) showed that the residue contained upper impurities and lower impurities in addition to desired product.
17. Move the filter funnel with product to a clean filtering flask.
18. Add acetone (100 ml) at room temperature to dissolve the filter cake. Note: Use a spatula to help dissolve the product.
19. Filter and add fresh acetone (100 ml) to dissolve the remaining filter cake and filter. Note: Only small amount of filter cake is typically left, with some of it stuck on the upper part of filter funnel.
20. Combine the filtrate and filter through Millipore 0.22 μm membrane filter (type GV) in glass filter assemblies.
21. Transfer the filtrate into a 500 ml round bottom flask. Rinse the filter flask with acetone (100 ml) and add to the 500 ml round bottom flask.
22. Evaporate the combined filtrate and wash to a foamy semisolid under high vacuum in a 40±5° C. water bath. Continue to dry under high vacuum in a 40±5° C. water bath for ~2 hrs to form a light yellow foamy semisolid (30 g, 85%). NMR (¹H) is consistent with structure. The product contained 2% water based on Karl Fischer analysis.

23. Store in the freezer at −20° C. or below.

80 g Scale: Procedure

A. Washing Molecular Sieves

1. Add molecular sieves (120 g) and chloroform-methanol 4:1 v/v (600 ml) to an appropriate size Erlenmeyer flask.
2. Swirl for ~3-5 minutes.
3. Decant the supernatant.
4. Add fresh chloroform-methanol 4:1 v/v (600 ml).
5. Swirl for ~3-5 minutes.
6. Decant the supernatant.
7. Add fresh chloroform-methanol 4:1 v/v (600 ml).
8. Swirl for ~3-5 minutes.
9. Decant the supernatant.
10. Transfer the washed molecular sieves into a 3 L-3-neck round bottom flask.

B. Reaction

1. Set up a 3 L-3-neck round bottom flask equipped with a heating mantle, a reflux condenser and a nitrogen-inlet tube.
2. Add chloroform-methanol 4:1 v/v (800 ml), N,N'-bis(2-hydroxyethyl)ethylene-diamine dioleoyl ester-2 HCl (80.0 g) to the flask.
3. Heat to reflux and continue to reflux until the reaction is ≧95% completed. Check the progress of the reaction with TLC (Silica Gel, chloroform-methanol 4:1 v/v, I$_2$-vapor and/or 5% sulfur acid in ethanol spray/charred). Note: It usually needs to reflux overnight (≧16 hrs).

Determination of the 95% completion of the reaction.

a. Set up a 4 dram vial
b. Add 0.5 g of N,N'-bis(2-hydroxyethyl)ethylenediamine dioleoyl ester•2 HCl (J8039) and 5 ml of chloroform-methanol 4:1 v/v.
c. Mix until all solid dissolves (solution #1)
d. Transfer 1 ml of the solution #1 into a 4-dram vial using a pipet.
e. Add 9 ml of chloroform-methanol 4:1 v/v, and mix. (solution #2). Note: The concentration of solution is 10% of solution #1.
f. Transfer 1 ml of the solution #2 to a 4-dram vial.
g. Add 1 ml of chloroform-methanol 4:1 v/v, and mix (solution #3). Note: The concentration of solution is 5% of solution #1.
h. Spot 3 µl of the reaction mixture on a silica gel TLC plate, and spot 3 µl of the solutions #2 and #3, respectively on the same plate using microcapillary pipets 1-5 µl.
i. Develop the TLC plate to 1 cm to the top.
j. Remove the TLC plate from the TLC tank and allow drying.
k. Place the plate in an iodine chamber for 1 hr or spray with 5% sulfuric acid in ethanol and char in an oven (150° C.) for 1 hr.
l. Compare the amount of starting material (J8039) left in the reaction mixture with the control solution #3. If they are same size and intensity, then the reaction is considered to be 95% completion.
4. Filter using Whatman glass microfibre filter on the top of Whatman #54 filter paper in a Buchner funnel and rinse the flask and filter cake with chloroform (400 ml).
5. Evaporate to dryness under high vacuum in a 35±5° C. water bath to form a light yellow oil (580 g).

C. Preparation of Silica Gel Column

1. Add Silica Gel (800 g; vol=~1.76 L) to a 4 L beaker.
2. Add sufficient chloroform to make slurry using an appropriate spatula to mix. Note: Make sure there are no air bubbles trapped in Silica Gel.
3. Add chloroform to the empty glass column. Note: ~2-3 inches above the bottom frit.
4. Pour the slurry to the column with the help of a spatula. Note: Make sure there are no air bubbles trapped inside Silica Gel.
5. Allow excess chloroform to elute out.
6. Tap repeatedly the side of the column to pack the Silica Gel and allow the excess chloroform to elute out.

D. Column Chromatography

1. Dissolve the oil from Step B5 in chloroform (120 ml) and charge onto the Silica Gel column.
2. Allow eluting until surface of the solution reaches the upper surface of silica gel.
3. Rinse the flask with chloroform three times (3×40 ml) and charge to the column, respectively. Note: After each wash, allow the surface of the solution reaches the upper surface of silica gel.
4. Elute (gravity) with chloroform (2 L), chloroform-methanol 97.5:2.5 v/v (4 L), 95:5 (4 L), 92.5:7.5 (4 L), 9:1 (4 L), 85:15 (4 L), and 8:2 (4 L). Collect two 4 L fractions. After that collect 250 ml fractions. The desired product starts to elute at chloroform-methanol 92.5:7.5 v/v step.
5. Check the purity of the individual fractions with TLC (Silica Gel, chloroform-methanol 4:1 v/v, I$_2$-vapor and/or 5% sulfuric acid in ethanol spray/charred). Note: Spot ~3 µl.
6. The fractions with purity ≧99% are pooled together every 5-10 fractions and evaporate to dryness.

Notes for Column Chromatography

It is better to combine 5-10 pure fractions (≧99%) and evaporate to dryness (Residue #1). Do semi-quantitative TLC as follows.

Transfer 10 to 15 mg of the Residue #1 using a SS spatula or other appropriate tool to a vial (1 dram or 4 dram vial).
Use a pipet, add 0.5 ml of chloroform.
Swirl until all the solids dissolve (solution #1).
Transfer 100 µl of the solution #1 into a separate vial (1 dram or 4 dram vial).
Add 900 µl of chloroform and mix (solution #2).
Spot 10 µl of solution #1 on a TLC plate using microcapillary pipettes 1-5 µl.
Spot 3 µl, 2 µl and 1 µl on the same TLC plate using microcapillary pipettes 1-5 µl.
Place the TLC plate in a TLC chamber containing chloroform-methanol 4:1 v/v (20 ml) and a sheet of filter paper in the back of the chamber.
Develop until the solvent front reaching ~1 cm to the top.
Remove the TLC plate from the chamber.
Allow the plate to dry.
Place the plate in an iodine chamber for ~1 hr or spray with 5% sulfuric acid in ethanol and char in an oven (150° C.) for ~1 hr.
Compare the impurity or combined impurities with the spots from 3 µl, 2 µl and 1 µl and estimate the purity.
Do the same thing to residue #2, #3, #4, etc.
Combine the residue with TLC purity ≧99%.
7. Combine the pure fractions and evaporate to an oil (<80 g).

E. Crystallization

1. Dissolve the oil from Step D7 in acetone (800 ml) in a round bottom flask.
2. Seal the flask and chill in dry ice/acetone bath for ~2-3 hrs. Note: Chill 300 ml of acetone in dry ice bath for rinsing.
3. Scrape the precipitate sticking on the side of glassware with an appropriate spatula.
4. Filter using 600-ml jacketed fritted glass funnel pre-cooled with glycol (−10° C. to −15° C.) into an appropriate flask (bottle).
5. Rinse with pre-cooled acetone from Step E2.
6. Move the jacketed filter funnel to a clean filtering flask.
7. Raise the glycol temp to room temperature.
8. Add acetone (~200 ml) at room temperature to dissolve the filter cake. Note: Use a spatula to help dissolving the filter cake.
9. Filter and then add fresh acetone (~200 ml) to dissolve remaining filter cake and filter.
10. Combine the filtrate and filter through 0.2 µm filter.

11. Rinse with acetone (~100 ml).
12. Evaporate the filtrate using Buchi rotavapor under high vacuum at 40±5° C. to a foamy semisolid.
13. Continue to dry under high vacuum at 40±5° C. for an additional 2.5±0.5 hrs. Note: The product melts near room temp and is hygroscopic.

F. Yield, Package and Storage
1. Weigh and calculate the yield.
2. Keep the product in the round bottom flask under nitrogen blanket, seal using a glass stopper with (polytetrafluoro-ethylene) PTFE sealing ring or sleeve and label the flask.
3. Store in a freezer at −20° C. or below.

All publications and patent applications mentioned in this specification are herein incorporated by reference to the same extent as if each individual publication or patent application was specifically and individually indicated to be incorporated by reference.

The disclosure now being fully described, it will be apparent to one of ordinary skill in the art that many changes and modifications can be made thereto without departing from the spirit or scope of the appended claims.

What is claimed is:

1. A method for preparing a compound of formula (I):

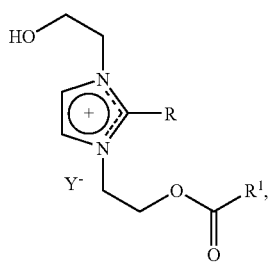

comprising the step of heating a compound of formula (II) between about 30° C. to about 60° C. in a trihaloalkyl/alcohol solvent, and in the presence of molecular sieves, to produce the compound of formula (I):

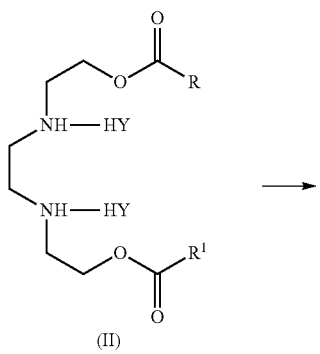

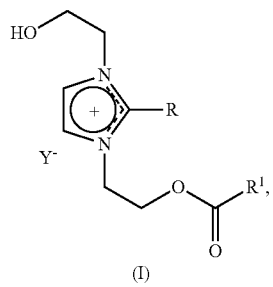

wherein:
R and $R^1$ are each independently a $C_{11}$-$C_{29}$ straight-chain aliphatic hydrocarbyl group;
and
Y is a halogen, acetate, succinate or citrate.

2. The method of claim 1, wherein R and $R^1$ are each:

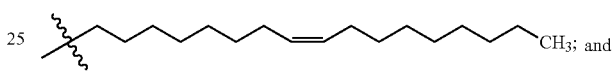

Y is chloro.

3. The method of claim 1, wherein the trihaloalkyl/alcohol solvent is about a 4:1 v/v mixture.

4. The method of claim 3, wherein the trihaloalkyl solvent is chloroform or bromoform; and the alcohol solvent is methanol, ethanol, propanol, or isopropanol.

5. The method of claim 4, wherein the trihaloalkyl solvent is chloroform; and the alcohol solvent is methanol.

6. The method of claim 1, wherein the molecular sieves are 4 Å molecular sieves and is present in about a 1:1 to about a 3:1 w/w ratio of 4 Å molecular sieves/compound of formula (II).

7. The method of claim 6, wherein the 4 Å molecular sieves is present in about a 1:2 w/w ratio of 4 Å molecular sieves/compound of formula (II).

8. The method of claim 1, wherein the compound of formula (II) is heated to about 55° C. for about 4 to about 24 hours.

9. The method of claim 1, further comprising purifying the compound of formula (I) by silica gel chromatography (with silica gel or silica gel pre-packed cartridges) and recrystallization from acetone.

10. The method of claim 1, wherein the compound of formula (I) has formula (III):

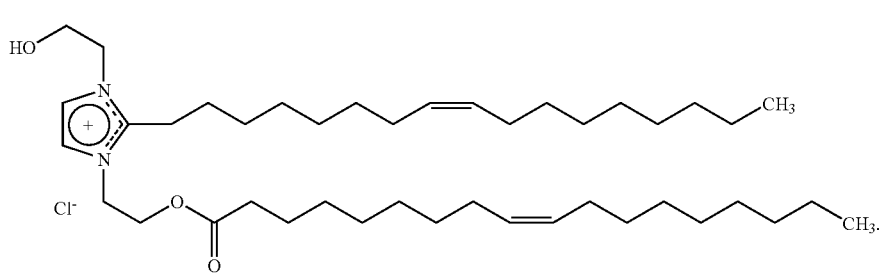

11. A method for preparing a compound of formula (I):

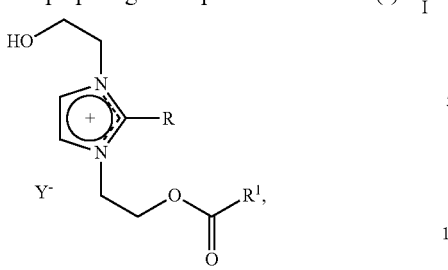

comprising the steps of:

a) protecting the secondary amino groups in the compound of formula (IV) to provide the compound of formula (V):

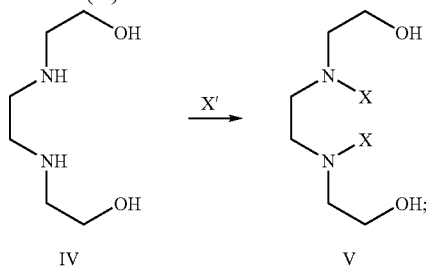

b) protecting the primary alcohol groups in the compound of formula (V) to provide the compound of formula (VI):

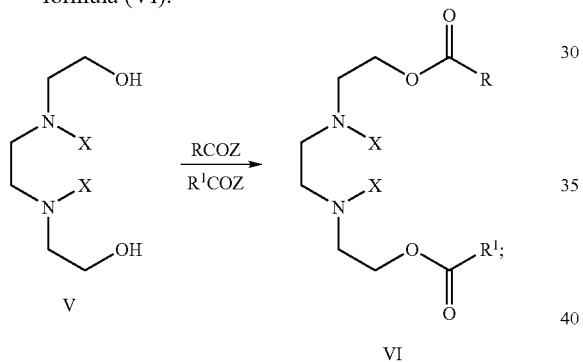

c) deprotecting the compound of formula (VI) to provide the compound of formula (II):

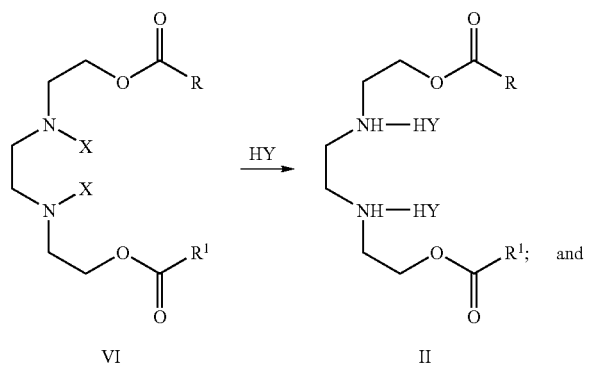

d) heating the compound of formula (II) between about 30° C. to about 60° C. in a trihaloalkyl/alcohol solvent, and in the presence of molecular sieves, to produce the compound of formula (I):

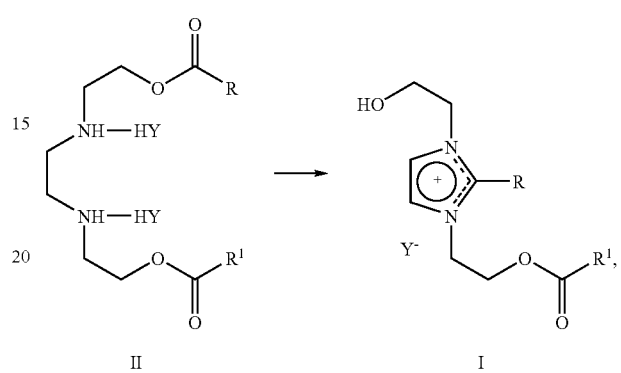

wherein:

R and $R^1$ are each independently a $C_{11}$-$C_{29}$ straight-chain aliphatic hydrocarbyl group;

X' is di-tert-butyldicarbonate ($(BOC)_2O$);

X is tert-butyloxycarbonyl (BOC);

Y is a halogen, acetate, succinate or citrate;

Z in OCOR or $OCOR^1$.

12. The method of claim 11, wherein R and $R^1$ are each:

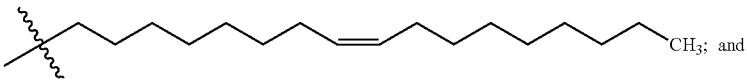

Y is chloro.

13. The method of claim 12, wherein the trihaloalkyl/alcohol solvent is about a 4:1 v/v mixture.

14. The method of claim 13, wherein the trihaloalkyl solvent is chloroform or bromoform; and the alcohol solvent is methanol, ethanol, propanol, or isopropanol.

15. The method of claim 14, wherein the trihaloalkyl solvent is chloroform; and the alcohol solvent is methanol.

16. The method of claim 12, wherein the molecular sieves are 4 Å molecular sieves and is present in about a 1:1 to about a 3:1 w/w ratio of 4 Å molecular sieves/compound of formula (II).

17. The method of claim 16, wherein the 4 Å molecular sieves is present in about a 1:2 w/w ratio of 4 Å molecular sieves/compound of formula (II).

18. The method of claim 12, wherein the compound of formula (II) is heated to about 55° C. for about 4 to about 24 hours.

19. The method of claim 12, further comprising purifying the compound of formula (I) by silica gel chromatography and recrystallization from acetone.

20. The method of claim 12, wherein the compound of formula (I) has formula (III):

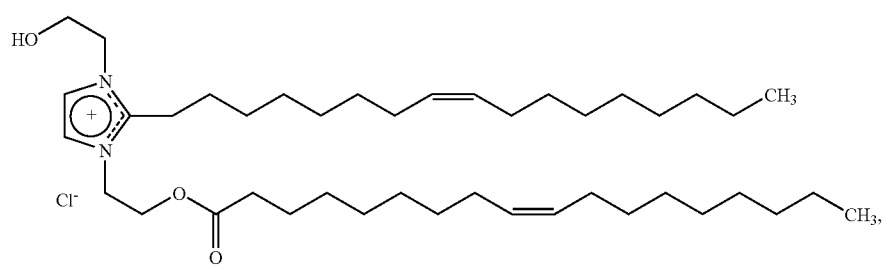
III
21. The method of claim 1, wherein R and R¹ are each independently a $C_{11}$-$C_{29}$ straight-chain aliphatic hydrocarbyl group.
* * * * *